United States Patent [19]

Chiesi et al.

[11] Patent Number: 5,162,573

[45] Date of Patent: Nov. 10, 1992

[54] VALPROIC AND (E)-2-VALPROENOIC ACID DERIVATIVES, AND PHARMACEUTICAL COMPOSITIONS THEREFROM

[75] Inventors: Paolo Chiesi; Vittorino Servadio; Flavio Villani, all of Parma, Italy

[73] Assignee: Chiesi Farmaceutici S.p.A., Parma, Italy

[21] Appl. No.: 63,643

[22] Filed: Jun. 17, 1987

[30] Foreign Application Priority Data

Jun. 19, 1986 [IT] Italy ............................... 20846 A/86

[51] Int. Cl.$^5$ ............................................... C07C 9/52
[52] U.S. Cl. ....................................... 560/224; 560/8; 560/263; 546/342; 548/530; 549/305; 549/375; 558/277
[58] Field of Search ........................... 560/263, 224, 8; 546/342; 548/530; 549/305, 375; 558/277; 514/549, 546, 423

[56] References Cited

U.S. PATENT DOCUMENTS 4,442,124  4/1984  Niklaus ........................... 560/263 X
4,654,370  3/1987  Marriott ............................. 514/547

FOREIGN PATENT DOCUMENTS 0018342  10/1980  European Pat. Off. .
114720    8/1984  European Pat. Off. .
2052500B  1/1981  United Kingdom .

*Primary Examiner*—Paul J. Killos
*Attorney, Agent, or Firm*—Bucknam and Archer

[57] ABSTRACT

2-Propyl-2-pentanoic acid (valproic acid) esters and (E)-2-propyl-2-pentenoic acid [(E)-2-valproenoic acid] esters surprisingly proved to have valuable properties, in that they show anticonvulsive and antiepileptic activities comparable with those of valproic acid, as well as an improved bioavailability and a markedly reduced toxicity.

15 Claims, No Drawings

VALPROIC AND (E)-2-VALPROENOIC ACID DERIVATIVES, AND PHARMACEUTICAL COMPOSITIONS THEREFROM

The present invention relates to 2-propyl-2-pentanoic acid (valproic acid) esters of formula (I):

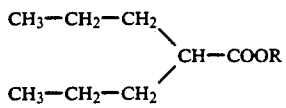

and (E)-2-propyl-2-pentenoic acid (E)-2-valproenoic acid esters of formula (II)

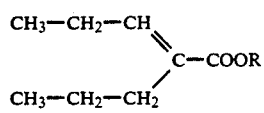

wherein R is an alkoxyalkyl, alkanoyloxyalkyl, aroyloxyalkyl, alkoxycarbonyloxyalkyl, aralkenoyloxyalkyl group, a mono- or bicyclic heterocycloalkyl group, which may be saturated or unsaturated and optionally substituted with a $C_1$-$C_4$ alkyl group or an oxo group; the above cited alkyl, alkoxyl and alkanoyl groups having straight or branched chain and containing 1 to 10 carbon atoms.

In formulae I and II, R preferably represents 2-methoxyethyl, 2-isopropoxyethyl, 2-butoxyethyl, 1-methyl-2-methoxyethyl, acetoxymethyl, 2-acetoxyethyl, pivaloyloxymethyl, 1- and 2-pivaloyloxyethyl, 2-propyl-pentanoyloxymethyl, 2-propyl-pentenoyloxymethyl, 2-(2-propylpentanoyloxy)ethyl, 2-(2-propyl-pentenoyloxy)ethyl, 1-ethoxycarbonyloxyethyl, 2-benzoyloxyethyl, 2-(3,4,5-trimethoxylbenzoyloxy)ethyl, 2-cinnamoyloxyethyl, 2-phthalidyl, 2-(N-succinimido)ethyl, (5-methyl-2-oxo-1,3-dioxolene-4-yl)methyl, 2-pyridylmethyl.

The following compounds: pivaloyloxymethyl 2-propylpentanoate, described in CH Pat. n. 635062 and 1-ethoxycarbonyloxyethyl 2-propylpentanoate, described in EP 114720, are specifically excluded from the present invention.

Valproic acid is an anticonvulsivant drug that has been widely used for a long time, as such or as sodium salt, in the treatment of epilepsy. In spite of its tested clinical efficacy, the compound actually presents serious side effects, that often prevent its use in the therapy. Valproic acid has been in fact associated with two kind of rare but extremely dangerous reactions, such as a serious hepatic insufficiency and teratogenic effects.

Another factor limiting the use of the drug is its kinetic profile, deriving from the particular chemicophysical characteristics of the compound.

As a matter of fact, valproic acid has a quite short half life that, besides causing consistent fluctuations in the plasmatic levels of the active ingredient, also involves a high number of daily administrations of drug (from a minimum of 3.4 to a maximum of 6 administrations/die).

The drawbacks caused by the therapy with valproic acid have stimulated more and more the search for new solutions in the last few years.

This research has aimed at obtaining new salts of the compound, in order to improve its stability in pharmaceutical compositions of pro-drugs of the active principle, in order to improve its bioavailability and to prolong its effect.

Among the numerous derivatives that have been obtained so far, the only one that seems to be a valid alternative to the starting compound is its main active metabolyte, trans-2-ene-valproic acid or 2-propyl-pentenoic acid, that proved to have a wide spectrum anticonvulsivant activity, a potency and a duration of action comparable to those of valproic acid, and remarkably reduced toxic effects.

Trans-2-ene-valproic acid is in fact totally devoid of teratogenic effects, and it is much better tolerated at hepatic level, thanks to a remarkably reduced hepatic concentration in comparison with valproic acid, after oral administration of equimolecular doses of the two active principles.

The pharmacokinetic behaviour of trans-2-ene-valproic acid is similar to the one of valproic acid.

The half life in man is slightly higher than that of the starting compound (12.5 hours in comparison with 9–10 hours of valproic acid), so that, for its use in the therapy, there are the same drawbacks of valproic acid.

It has now been found, and it is one of the objects of the present invention, that new esters of valproic acid and of valproenoic acid are surprisingly endowed with particularly favourable characteristics, since they exhibit an anticonvulsivant and antiepileptic activity that can be compared with that of valproic acid, together with a better bioavailability and a remarkably reduced toxicity.

Thanks to these characteristics, the new derivatives of formula (I) and (II) may therefore be effectively used in the therapy of epileptic disorders.

Novel compounds of formulae I and II may be prepared by reacting the starting compound, i.e. valproic acid (formula I, R=H) or (E)-2-valproenoic acid (formula II, R=H) with at least an equivalent molar amount of a halo-derivative of formula RX, wherein R has the above defined meanings and X is preferably chlorine or bromine.

The reaction is usually carried out in an inert organic solvent which does not negatively affect said reaction, in the presence of a suitable amount of an appropriate standard alkali substance and of a catalyst.

The reaction is generally effected at a temperature ranging from about 0° C. to the solvent's boiling temperature, for a time from about 0,5 to about 24 hours.

Although any inert organic solvent may be used, aprotic polar organic solvents such as dimethylformamide, acetone, dioxane, tetrahydrofuran are generally preferred.

Among the appropriate standard alkali substances which may be used in the process, there are alkali and alkali-earth metal oxides, bicarbonates and carbonates, such as magnesium oxide, potassium bicarbonate, sodium bicarbonate, potassium carbonate and magnesium carbonate, and also tertiary amines such as triethylamine, N,N-dimethylaniline and pyridine; potassium carbonate being preferred.

The employed standard alkali substance must be present in a sufficient amount to neutralize the halohydric acid which is formed during the reaction.

Alkali and alkali-earth metal iodides may be used as catalysts in the reaction, potassium iodide being preferred.

According to an alternative process, valproic and (E)-2-valproenoic acid chlorides may be treated with the corresponding alcohol derivatives of the kind ROH, wherein R has the above defined meanings.

In this case, the reaction is carried out under conditions similar to those of the above process, of course avoiding the use of protic solvents.

Aliphatic or aromatic tertiary amines may be used to play the role of both solvent and base to neutralize the halohydric acid which is formed during the reaction.

A third particularly advantageous process to obtain alkylidene-bis-valproates or alkylidene-bis-(E)-2-valproenates (compounds of formula I or II wherein R is —Ch$_2$—O$_2$CCH(C$_3$H$_7$)$_2$ or —(CH$_2$)$_2$—O$_2$CCH(C$_3$H$_7$)$_2$, consists in treating valproic or (E)-2-valproenoic acids with an alkyl dihalide of the type X—(CH$_2$)n—X, (wherein n=1–5 and X=Cl, Br, I).

The reaction is carried out in a biphasic system consisting of an alkali aqueous solution of the starting compound and of the alkyl dihalide, which plays the double role of reagent and solvent, in the presence of an appropriate catalyst.

The reaction is generally carried out at a temperature from 10° to 70° C., for a time ranging from 1 to 24 hours.

Inorganic bases such as alkali and alkali-earth metal hydroxides, oxides, bicarbonates and carbonates, for example sodium hydroxide, potassium hydroxide, sodium bicarbonate, potassium carbonate, magnesium carbonate, may be employed as alkali substances.

As catalysts, quaternary alkylammonium salts, such as tetraethylammonium bromide, tetrabutylammonium hydrogenosulfate, tetrabutylammonium iodide, etc. are particularly preferred.

In order to promote the reaction, alkali or alkali-earth metal iodides may be further used, preferably potassium iodide. The starting materials necessary for preparing the derivatives object of the present invention are commercially available or may be prepared according to methods known in the literature.

Some non-limiting examples of the processes for preparing the compounds of the invention are reported hereinbelow.

EXAMPLE 1

2'-Acetoxyethyl 2-propyl-pentanoate (valproic acid 2-acetoxyethyl ester) (compound n. 3)

20.18 g (0.14 mole) of 2-n-propyl-pentanoic acid (valproic acid) were dissolved in 150 ml of dimethylformamide. After heating to 70°–100° C., 13,82 g (0.1 mole) of potassium carbonate were added. The mixture was stirred for about 10 minutes, then 1.66 g (0.01 mole) of potassium iodide followed by 17.16 g (0.14 mole) of 2-acetoxyethyl chloride were added dropwise. Stirring was continued for about 3 hours at 80°–100° C., then the mixture was left to cool to room temperature and about 600 ml of water were added. The mixture was extracted with ethyl acetate and the organic layer was washed with a sodium bicarbonate saturated solution, then with water till neutral.

The organic solution was dried over sodium sulfate and the solvent was evaporated off under vacuum, in rotary evaporator.

The residual oil was fractionally distilled under vacuum, to yield a fraction distilling at 83° C. at 0.1 mbar.

22.57 g of compound (70% yield) were obtained.

MF=C$_{12}$H$_{22}$O$_4$; MW=230.308

Elemetal analysis and spectroscopic data (IR, NMR) confirm the structure of the compound.

By the same procedure, again using 2-propyl-pentanoic acid as the starting material, compounds n. 4 to n. 8, were obtained, whose characteristics are reported in table 1.

Analogously, but starting from 2-propyl-2-pentenoic acid, compounds n. 9 to n. 14 were obtained, whose characteristics are reported in table 2.

EXAMPLE 2

2-(2-propylpentanoyloxy)ethyl 2-propylpentanoate (oxyethylene valproyl-valproate) (compound n. 15)

176.58 g (0.520 mole) of (C$_4$H$_9$)$_4$N$^+$HSO$_4$ and subsequently 800 ml of 1,2-dichloroethane were added to a solution of 150 g (1.040 mole) of 2-propyl-pentanoic acid (valproic acid) in 110.22 ml (1.092 mole) of 30% NaOH. After heating to reflux (T=74° C.), 18.13 g (0.109 mole) of KI were added, keeping reflux for 20 hours. After cooling to room temperature, the two phases were separated and the aqueous layer was extracted with about 300 ml of 1,2-dichloroethane. The 1,2-dichloroethane solutions were combined, washed many times with water, then with 10% NaOH and again with water till neutral. The organic phase was washed many times with 0.5N HCl, then with water till neutral.

The mixture was dried with Na$_2$SO$_4$, filtered, decolorized with bleaching clay, filtered and the solvent was evaporated. The obtained oil was treated with ethyl ether, and the solid part was removed by filtration. Solvent was evaporated off. The residual oil was subjected to distillation under vacuum and the fraction distilling at T=93° C. at pression=1 mbar was recovered. 71.51 g of compound (43.73%) were obtained.

M.F.=C$_{18}$H$_{34}$O$_4$; M.W. 314.47

Elemental analysis and spectroscopic data (IR, NMR) confirm the structure of the compound.

By a procedure similar to the one discribed in example 2, using valproic acid and methylene chloride as the starting compounds, compound n. 16, i.e. 2-propylpentanoyloxymethyl 2-propyl-pentanoate, was obtained, whose characteristics are illustrated in table 1.

EXAMPLE 3

Pivaloyloxymethyl 2-propyl-2-pentenoate (E cis) (valproenoic acid pivaloyloxymethyl ester) (Compound n. 17)

13.82 g (0,1 mole) of K$_2$CO$_3$ were added to a solution of 14.22 g (0.1 mole) of (E)-2-propyl-2-pentenoic acid in 400 ml of acetone, heated to 40°–50° C., and subsequently 15.36 g (0.102 mole) of chloromethyl pivalate were added dropwise, during 10 minutes. The mixture was refluxed for about 3 hours and, after cooling to room temperature, 2 l of water were added. The mixture was repeatedly extracted with ethyl acetate, the combined organic layers were wached with a NaHCO$_3$ saturated solution, then with water till neutral.

After drying over Na$_2$SO$_4$, solvent was evaporated off to give an oily residue which was distilled under vacuum. The fraction distilling at 85° C. at 1.3 mbar was recovered.

18.71 g of compound (73% yield) were obtained.

M.F.=C$_{14}$H$_{24}$O$_4$; M.W.=256.33

Elemental analysis and spectroscopic data (IR, NMR) confirm the structure of the compound.

By a procedure similar to the one described in example 3, again using (E)-2-propyl-pentenoic acid as the starting compound, compounds n. 18 to n. 21, whose characteristics are reported in table 2, were obtained.

EXAMPLE 4

2-(2',5'-dione-pyrrolidine-1-yl)ethyl 2-propyl-2-pentenoate (E cis) valproenoic acid 2-(N-succinimido) ethyl ester)

22.49 g (0.14 mole) of (E)-2-propyl-2-pentenoic acid chloride were slowly added to a solution of 19.75 g (0.138 mole) of 1-(2'-hydroxyethyl)-pyrrolidine-2,5-dione in 100 ml of pyridine heated at 35°–45° C. The mixture was left at 40°–50° C, for about 1 hour, then 500 ml of water were added. The mixture was extracted repeatedly with ethyl acetate and the combined organic layers were washed with a NaHCO$_3$ saturated solution, then with water till neutral. After drying over Na$_2$SO$_4$, solvent was evaporated and an oil was obtained which was distilled under vacuum. The fraction distilling at temperature 145° C. at a 0.18 mbar pressure was recovered.

29.13 g of compound (78% yield) were obtained.
MF=C$_{14}$H$_{21}$NO$_4$; M=267.32

By a similar procedure, using (E)-2-propyl-2-pentenoic acid chloride and the corresponding hydroxyalkyl derivatives as the starting materials, compounds n. 23 to n. 27 were obtained, whose characteristics are reported in table 2.

TABLE 1

Compounds of formula:

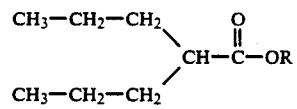

| Comp. | R | B.P. °C./mbar | M.F. | M.W. | CHF |
|---|---|---|---|---|---|
| 3 | —(CH$_2$)$_2$O$_2$C—CH$_3$ | 83/0,1 | C$_{12}$H$_{22}$O$_4$ | 230,308 | 1312 |
| 4 | —CH(CH$_3$)—O$_2$C—C(CH$_3$)$_3$ | 80/0,1 | C$_{15}$H$_{28}$O$_4$ | 272,37 | 1314 |
| 5 | —(CH$_2$)$_2$—O$_2$C—C(CH$_3$)$_3$ | 106/0,1 | C$_{15}$H$_{28}$D$_4$ | 272,37 | 1313 |
| 6 | —(CH$_2$)$_2$—O$_2$COC$_2$H$_5$ | 100/0,1 | C$_{13}$H$_{24}$O$_5$ | 260,32 | 1308 |
| 7 | 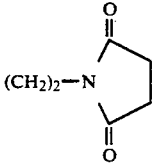 | 127/0,1 | C$_{13}$H$_{20}$O$_5$ | 256,30 | 1315 |
| 8 | | 132/0,2 | C$_{14}$H$_{23}$NO$_4$ | 269,35 | 1359 |
| 15 | —(CH$_2$)$_2$—O$_2$CCH(C$_3$H$_7$)$_2$ | 93/1 | C$_{18}$H$_{34}$O$_4$ | 314,47 | 1352 |
| 16 | —CH$_2$—O$_2$CCH(C$_3$H$_7$)$_2$ | 100/0,1 | C$_{17}$H$_{32}$O$_4$ | 300,44 | 1355 |

TABLE 2

Compounds of formula:

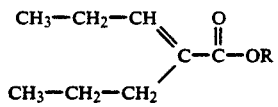

| Comp. | R | B.P. °C./mbar | MF | M.W. | CHF |
|---|---|---|---|---|---|
| 9 | —(CH$_2$)$_2$—O$_2$C-Ph | 155/0,2 | C$_{17}$H$_{22}$O$_4$ | 290,35 | 1406 |
| 10 | —(CH$_2$)$_2$—O$_2$C—CH=CH-Ph | 187/0,1 | C$_{19}$H$_{24}$O$_4$ | 316,38 | 1408 |
| 11 | —(CH$_2$)$_2$—O$_2$C-Ph-3,4,5(OCH$_3$)$_3$ | 207/0,3 | C$_{20}$H$_{28}$O$_4$ | 332,42 | 1409 |
| 12 | —(CH$_2$)$_2$—O$_2$CCH$_3$ | 102/0,2 | C$_{12}$H$_{20}$O$_4$ | 228,28 | 1415 |
| 13 | —(CH$_2$)$_2$—O$_2$C(CH$_3$)$_3$ | 106/0,18 | C$_{15}$H$_{26}$O$_4$ | 270,36 | 1413 |
| 14 | —(CH$_2$)$_2$—O$_2$COC$_2$H$_5$ | 116/0,25 | C$_{13}$H$_{22}$O$_5$ | 258,31 | 1414 |
| 17 | —CH$_2$—O$_2$C—C(CH$_3$)$_3$ | 85/1,3 | C$_{14}$H$_{24}$O$_4$ | 256,33 | 1378 |
| 18 | 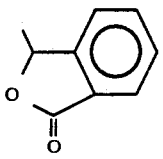 | 170/0,4 | C$_{16}$H$_{18}$O$_4$ | 274,30 | 1410 |
| 19 | —CH$_2$O$_2$CCH$_3$ | 86/0,3 | C$_{11}$H$_{18}$O$_4$ | 214,25 | 1416 |

TABLE 2-continued

Compounds of formula:

$$CH_3-CH_2-CH_2 \diagdown \atop CH_3-CH_2-CH_2 \diagup C-C(=O)-OR$$

with C=CH(CH_2CH_3) on top carbon

| Comp. | R | B.P. °C./mbar | MF | M.W. | CHF |
|---|---|---|---|---|---|
| 20 | —CH(CH$_3$)—O$_2$CC(CH$_3$)$_3$ | 62/0,3 | C$_{15}$H$_{26}$O$_4$ | 270,36 | — |
| 21 | —CH$_2$—[cyclic carbonate with CH$_3$] | | C$_{13}$H$_{18}$O$_5$ | 254,27 | 1418 |
| 22 | —CH$_2$CH$_2$—N[succinimide] | 145/0,8 | C$_{14}$H$_{21}$NO$_4$ | 267,32 | 1417 |
| 23 | —(CH$_2$)$_2$—O—(CH$_2$)$_3$CH$_3$ | 84/0,1 | C$_{14}$H$_{26}$O$_3$ | 242,35 | 1411 |
| 24 | —CH(CH$_3$)—CH$_2$—OCH$_3$ | 63/0,1 | C$_{12}$H$_{22}$O$_3$ | 214,30 | 1412 |
| 25 | —(CH$_2$)$_2$—OCH(CH$_3$)$_2$ | 78/0,1 | C$_{13}$H$_{24}$O$_3$ | 228,32 | 1407 |
| 26 | —CH$_2$—CH$_2$—O—CH$_3$ | 67/0,1 | C$_{11}$H$_{20}$O$_3$ | 200,27 | 1420 |
| 27 | —CH$_2$-[pyridyl] | 108/0,1 | C$_{14}$H$_{19}$NO$_2$ | 233,30 | 1421 |

The compounds of formula I and II have been subjected to a preliminar toxico-pharmacological study.

Toxicity

The toxicity after single administration has been determined by the oral route in mice.

All the compounds showed an approximate LD$_{50}$ value higher than 2000 mg/kg, according to interpolation on Probits diagram.

Anticonvulsivant activity

The determination of the anticonvulsivant activity has been carried out by the pentetrazol convulsions test in mice.

Male Crl: CD-1 mice (Charles River-Italy) housed in standard conditions since at least 7 days and fasting (water ad libitum) for 18 hours before the test, were administered subcutaneously, in the dorsal area, with a 0,9% pentetrazole saline solution, in an amount of 10 ml/kg (90 mg/kg).

Immediately after the injection of the convulsivant agent, the animals were kept in single boxes and observed for 30 minutes for the appearance of clonic convulsion. The presence of possible deaths or neurotoxicity symptoms was moreover assessed before the pentetrazol injection.

For the evaluation of the anticonvulsivant activity, the ratio of protected animals versus controls was recorded and AUC values (% protection×hours), both total and relative to the 8-16 hours time interval from treatment, were determined by the trapezoid method in order to evaluate the persistance of activity in time.

The obtained results expressed as AUC values are reported in tables 3 and 4 concerning respectively the valproic acid derivatives and the (E)-2-valproenoic acid derivatives of the present invention.

As reference compound, sodium valproate has been used in the first group at the maximum administerable dose, and valproenoic acid in the second group.

TABLE 3

Anticonvulsivant activity of compounds of general formula I (valproic acid derivatives): AUC values (area under the curve showing the percent protection in time against the convulsivant agent).

| Compounds | Code (CHF) | Dose mg/kg | Dose mmol/kg | Protection from convulsions onset AUC (protection % × h) total | Protection from convulsions onset AUC (protection % × h) 8–16 h |
|---|---|---|---|---|---|
| 3 | 1312 | 1070 | 4.6 | 609 | 116 |
| 4 | 1314 | 1265 | 4.6 | 625 | 240 |
| 5 | 1313 | 1265 | 4.6 | 519 | 200 |
| 6 | 1308 | 1197 | 4.6 | 621 | 148 |
| 7 | 1315 | 1190 | 4.6 | 681 | 144 |
| 8 | 1359 | 1251 | 4.6 | 647 | 116 |
| 15 | 1352 | 1461 | 4.6 | — | — |
| 16 | 1355 | 1395 | 4.6 | 751 | 252 |
| sodium valproate | — | 506 | 3.1 | 351 | 24 |

TABLE 4

Anticonvulsivant activity of compounds of the general formula II (valproenoic acid derivatives): AUC values.

| Compounds | Code (CHF) | Dose mg/kg | Dose mmol/kg | Protection from convulsions onset AUC (protection % × h) total | Protection from convulsions onset AUC (protection % × h) 8–16 h |
|---|---|---|---|---|---|
| 9 | 1406 | 1347 | 4.6 | 181 | 28 |
| 10 | 1408 | 1217 | 4.6 | 341 | 112 |
| 19 | 1416 | 994 | 4.6 | 208 | 58 |
| 22 | 1417 | 1420 | 4.6 | 240 | 28 |

TABLE 4-continued

Anticonvulsivant activity of compounds of the general formula II (valproenoic acid derivatives): AUC values.

| Compounds | Code (CHF) | Dose mg/kg | Dose mmol/kg | Protection from convulsions onset AUC (protection % × h) total | 8–16 h |
|---|---|---|---|---|---|
| 27 | 1421 | 1101 | 4.6 | 122 | 58 |
| valproenoic acid | — | 592 | 4.2 | 284 | 36 |

The compounds of formula I and II exhibit a positive pharmacological interest.

All the valproic acid derivatives (table 3) proved to be remarkably more active than the starting compound with a remarkably longer persistance of the activity itself as showed by the increase of the AUC values inherent to prolonged periods (8–16 hours from treatment).

The valproenoic acid derivatives (table 4), although showing an anticonvulsivant activity comparable to that of the starting compound, as showed by the AUC values increase inherent to prolonged period, are generally characterized by a longer duration of action of the activity itself.

The two combined effects, decrease of the activity peak and prolonging of activity in time, have considerable therapeutic advantages, in that a longer duration of action is accompanied by a reduction of side-effects, particularly of the neurotoxic effects related to the presence of high blood levels of valproic acid.

Another object of the present invention is provided by pharmaceutical compositions which may be administered by oral route, to be used in therapy for the treatment of epileptic conditions, said compositions containing as the active ingredient one compound of formulae I or II, in combination with at least a pharmaceutically acceptable excipient.

Examples of said compositions, which may be prepared according to conventional methods, preferably consist in soft-gelatin capsules, in which the active ingredient is present dissolved in a vegetal or mineral oil, or hard-gelatin capsules, in which the active ingredient is present in admixture with a gelifying agent, such as for instance precipitated silica and fatty substances having melting point higher than 50°–60° C.

The unitary dose for the above discribed formulations will vary from 200 to 1000 mg of active ingredient.

Another type of pharmaceutical composition consists in suspensions or emulsions in which the active ingredient is present in concentrations varying from 20 to 50%, vehiculated in appropriate syrup excipients.

Some exemplificative formulations are reported hereinbelow.

| A. Formulation in soft-gelatin capsules Composition having 3 different dosages: | | | |
|---|---|---|---|
| Compound n. 3 | 1.000 | 750 | 500 mg |
| Vegetal oil | 170 | 85 | 42.5 |
| B. Formulation in hard-gelatin capsules Composition having 2 different dosages: | | | |
| Compound n. 24 | | 600 | 300 mg |
| Precipitated silica | | 46.2 | 23.1 |
| Dipalmitostearic monoditriglicerides | | 50 | 25 |

We claim:
1. A compound of formula

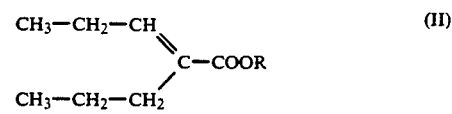

wherein R is alkoxyalkyl, alkanoyloxyalkyl, aroyloxyalkyl, alkoxycarbonyloxyalkyl, aralkenoyloxyalkyl, 2-phthalidyl, 2-(N-succinimido)ethyl, (5-methyl-2-oxo-1,3-dioxolene-4-yl)methyl, 2-pyridylmethyl group, said R being unsubstituted or substituted with $C_1$–$C_4$ alkyl or an oxo group; said alkyl, alkoxyl and alkanoyl groups having straight or branched chain and containing 1 to 10 carbon atoms.

2. A compound according to claim 1, which is:
2'-benzoyloxyethyl (E)-2-propyl-2-pentenoate;
2'-cinnamoyloxyethyl (E)-2-propyl-2-pentenoate;
2'-(3,4,5-trimethoxybenzoyl)-ethyl (E)-2-propyl-2-pentenoate;
2'-acetoxyethyl (E)-2-propyl-2-pentenoate;
2'-pivaloyloxyethyl (E)-2-propyl-2-pentenoate;
2'-ethoxycarbonyloxyethyl(E)-2-propyl-2-pentenoate;
pivaloyloxymethyl (E)-2-propyl-2-pentenoate;
phthalidyl (E)-2-propyl-2-pentenoate;
acetoxymethyl (E)-2-propyl-2-pentenoate;
1'-pivaloyloxyethyl (E)-2-propyl-2-pentenoate;
(5-methyl-2-oxo-1,3-dioxolene-4-yl)-methyl (E)-2-pentenoate;
2'(2,5-dione-1-pyrrolidine)-ethyl (E)-2-propyl-2-pentenoate;
2'-n-butyloxyethyl (E)-2-propyl-2-pentenoate;
1'-methoxymethylethyl (E)-2-propyl-2-pentenoate;
2'-isopropyloxyethyl (E-2)-propyl-2-pentenoate;
2'-methoxyethyl (E)-2-propyl-2-pentenoate;
2-pyridylmethyl (E)-2-propyl-2-pentenoate.

3. A compound of formula

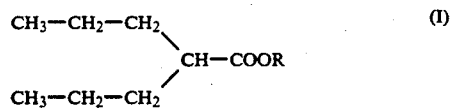

wherein R is alkanoyloxyalkyl, aroyloxyalkyl, alkoxycarbonyloxyalkyl, aralkenoyloxyalkyl, 2-phthalidyl, 2-(N-succinimido)ethyl, (5-methyl-2-oxo-1,3-dioxolene-4-yl)methyl, 2-pyridylmethyl group, said R being unsubstituted or substituted with $C_{1-4}$ alkyl or an alkyl or an oxo group; said alkyl, alkoxyl and alkanoyl groups having straight or branched chain and containing 1 to 10 carbon atoms, with the proviso that, in said compound of general formula (I), R is not 1-ethoxycarbonyloxyethyl or pivaloxymethyl.

4. A compound according to claim 3 which is:
2'-acetoxyethyl 2-propyl-pentanoate;
1'-pivaloyloxyethyl 2-propyl-pentenoate;
2'-pivaloyloxyethyl 2-propyl-pentenoate;
2'-ethoxycarbonyloxyethyl 2-propyl-pentenoate;
(5-methyl-1,3-dioxolene-2-oxo-4-yl)-methyl 2-propyl-pentanoate;
2'-(2,5-dione-pyrrolidine-1-yl)-ethyl 2-propyl-pentanoate;
2-propyl-pentanoyloxymethyl 2-propyl-pentanoate.

5. A diester from valproic acid of formula

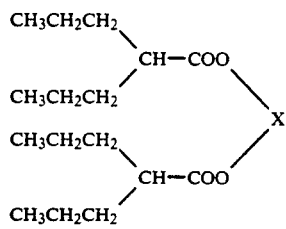

wherein X is (a) —CH$_2$—.

6. A composition for oral administration containing as the active ingredient a compound of formula II according to claim 1 wherein R is —(CH$_2$)$_2$—O$_2$C—Ph; —(CH$_2$)$_2$—O$_2$C—CH=CH—Ph; —CH$_2$O$_2$CCH$_3$;

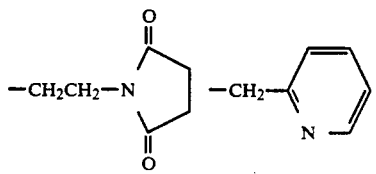

and at least one pharmaceutically acceptable excipient;

7. A composition for oral administration containing as the active ingredient a compound of formula I according to claim 3 wherein R is —(CH$_2$)$_2$—O$_2$C—Ph; —(CH$_2$)$_2$—O$_2$C—CH=CH—Ph; —CH$_2$O$_2$CCH$_3$;

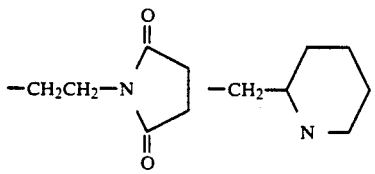

and at least one pharmaceutically acceptable excipient.

8. A pharmaceutical composition according to claim 5 for oral administration containing as the active ingredient 200–1,000 mgs of the compound 2-propyl-pentanoyloxymethyl 2-propyl-pentanoate in a soft gelatin capsule with a vegetable or mineral oil or 200–1,000 mgs of said compound in a hard gelatin capsule with a gelifying agent.

9. A pharmaceutical composition according to claim 5 containing as the active ingredient 2-propyl-pentanoyloxymethyl 2-propyl pentanoate in the form of a suspension or emulsion containing 20–50% of said active ingredient and at least one excipient.

10. A pharmaceutical composition for oral administration, containing as the active ingredient a compound according to claim 1 in combination with a pharmaceutically acceptable excipient.

11. A pharmaceutical composition according to claim 10 in unit dosage form consisting of soft-gelatin capsules or hard-gelatin capsules.

12. A pharmaceutical composition according to claim 10 in form of a suspension or an emulsion.

13. The method of treating epileptic conditions which consists of administering to a subject in need of treatment a composition containing as the active ingredient a compound of formula

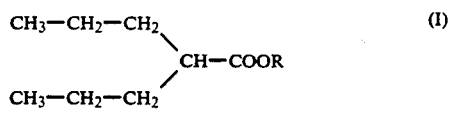

wherein R is alkanoyloxyalkyl, aroyloxyalkyl, alkoxycarbonyloxyalkyl, aralkenoyloxyalkyl, 2-phthalidyl, 2-(N-succinimido)ethyl, (5-methyl-2-oxo-1,3-dioxolene-4-yl)methyl, 2-pyridylmethyl group, said R being unsubstituted or substituted with C$_1$–C$_4$ alkyl or an oxo group; said alkyl, alkoxyl and alkanoyl groups having straight or branched chain and containing 1 to 10 carbon atoms, with the proviso that, in said compound of general formula (I), R is not 1-ethoxycarbonyloxyethyl or pivaloyloxymethyl, said composition containing 200–1,000 mgs of said compound and at least one excipient.

14. The method of treating epileptic conditions which consists of administering to a subject in need of treatment a composition containing as the active ingredient a compound of formula

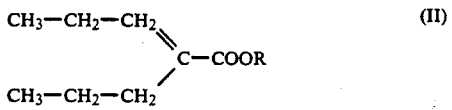

wherein R is alkoxyalkyl, alkanoyloxyalkyl, aroyloxyalkyl, alkoxycarbonyloxyalkyl, aralkenoyloxyalkyl, 2-phthalidyl, 2-(N-succinimido)ethyl, (5-methyl-2-oxo-1,3-dioxolene-4-yl)methyl, 2-pyridylmethyl group, said R being unsubstituted or substituted with C$_1$–C$_4$ alkyl or an oxo group; said alkyl, alkoxyl and alkanoyl groups having straight or branched chain and containing 1 to 10 carbon atoms, said composition containing 200–1,000 mgs of said compound and at least one excipient.

15. The method of treating epileptic conditions which consists of administering to a subject in need of treatment a composition containing as the active ingredient a compound of formula

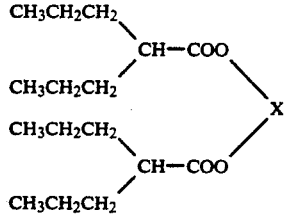

wherein X is (a) —CH$_2$—.

* * * * *